United States Patent [19]

Brown

[11] Patent Number: Plant 6,842

[45] Date of Patent: Jun. 6, 1989

[54] AGLAONEMA 'QUEEN OF SIAM'

[75] Inventor: B. Frank Brown, Palm Bay, Fla.

[73] Assignee: Weyerhaeuser Company, Tacoma, Wash.

[21] Appl. No.: 153,735

[22] Filed: Feb. 8, 1988

[51] Int. Cl.[4] ..... A01H 5/00

[52] U.S. Cl. ..... Plt./88

[58] Field of Search ..... Plt./88

[56] References Cited

PUBLICATIONS

Bailey, L. H. & E. Z., 1976, *Hortus Third,* Macmillian, New York.

Brown, B. F., 1980, New Discoveries, New Hybrids and Related Knowledge, *Aroideana,* Publication of the International Aroid Society 3(4): 120–126.

Brown, B. F., 1984, The New Aglaonemas of Thailand, *Aroideana,* 7(2): 43–52.

Graf, A. B., 1978, *Tropica—Color Cyclopedia of Exotic Plants and Trees,* Rohers Co., East Rutherford, New Jersey.

Jervis, R. N., 1987, *Florida Ornamental Plants, Aglaonema Growers Notebook,* Clearwater, Fl.

Henny, R. J., n.d. *Foliage Plant Breeding Profile III, Aglaonema nitidum,* 'Curtisii', Agricultural Research and Education Center, University of Florida, Apopka, Fl.

*Primary Examiner*—Robert E. Bagwill

[57] ABSTRACT

A new and distinct variety of Aglaonema characterized by compact growth habit with large four color variegated leaves.

3 Drawing Sheets

The present invention relates to a new and distinct hybrid of Aglaonema which originated as a cross-pollination of *Aglaonema commutatum* cv. 'Tricolor' (*A. marantifolium* var. tricolor) and *Aglaonema nitidum* cv. 'Curtisii' hybrid 'Ernesto's Favorite', in the Araceae family, commonly known as "Chinese Evergreen".

This new Aglaonema is the result of deliberate cross-pollination of the plants listed above performed by the inventor in a shade house adjacent to his home in Valkaira, Fla. in 1985. This new hybrid was selected out and isolated for further evaluation because it had distinct, highly attractive, and very colorful variegated leaves. The new variety has been reproduced by asexual propagation (division). Each of the progeny exhibits identical characteristics to the original mother plant establishing this hybrid as reproducable and true to type.

This new hybrid is unlike any Aglaonema commercially available nor like any of those described by Graf, Bailey, or Jervis (see reference list) as evidenced by the following unique combination of characteristics:

(1) Attractive and distinct variegated coloration of the leaves that consists of four colors on the upper leaf surface.

Light grey-green central area that occupies about 50% to 70% of the leaf surface.

Dark green margins and also blotches and spots.

Medium grey-green blotches and spots between margins and central area that create a marbled effect.

Bright yellow-green markings and spots on the midrib.

(2) The robust suckering habit gives the plant a compact and full appearance; the large oblong leaves are another exceptional and distinct characteristic of this hybrid.

BRIEF DESCRIPTION OF THE PHOTOGRAPHS

DETAILED PLANT DESCRIPTION

Figure 1:
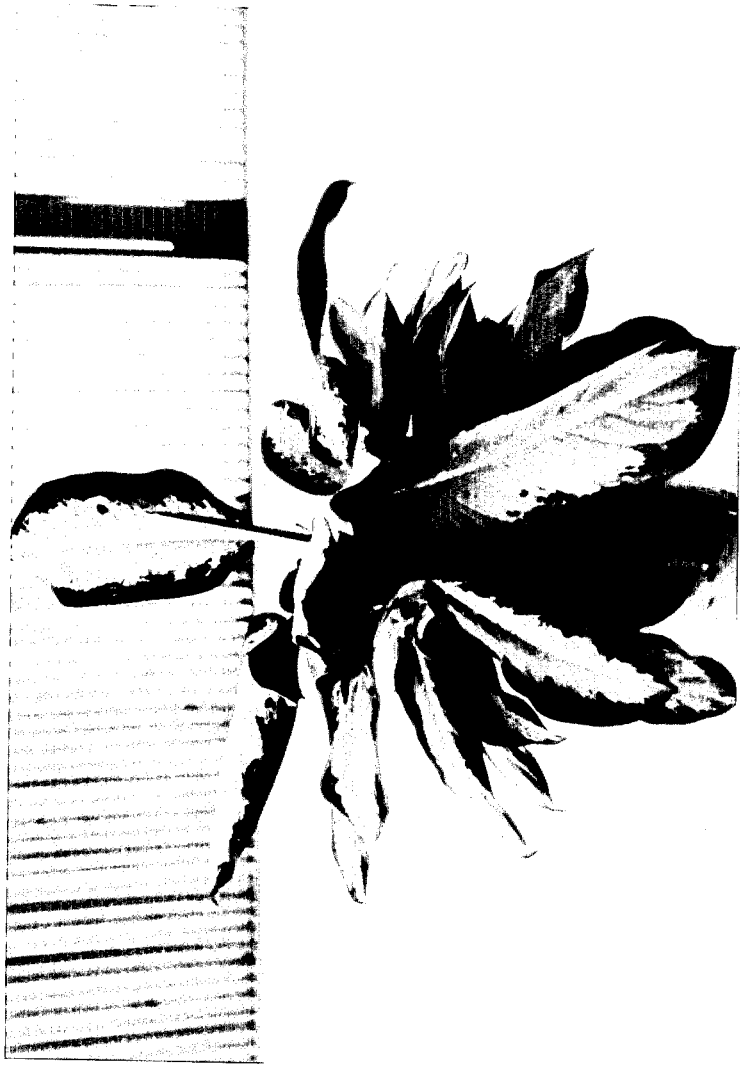
FIG. 1 is an unpruned 2 year old individual plant of the new variety showing its suckering habit, compactness, large leaves and robust appearance.
Figure 2:
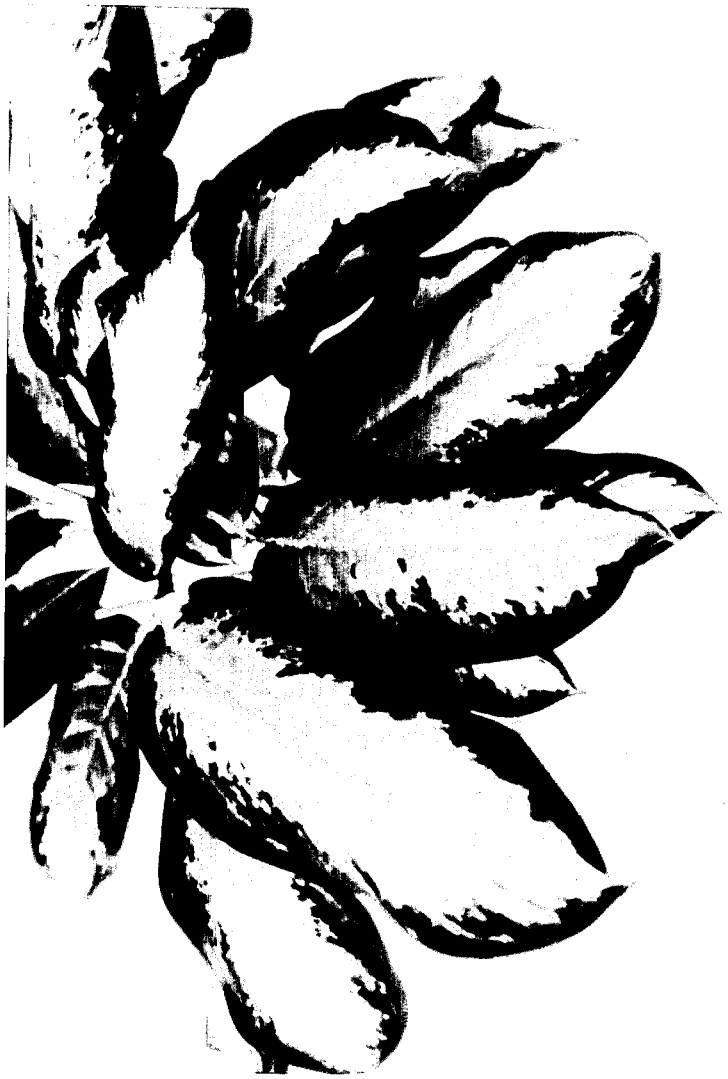
FIG. 2 is a closeup showing the four color variegation of the upper surface of mature leaves.
Figure 3:
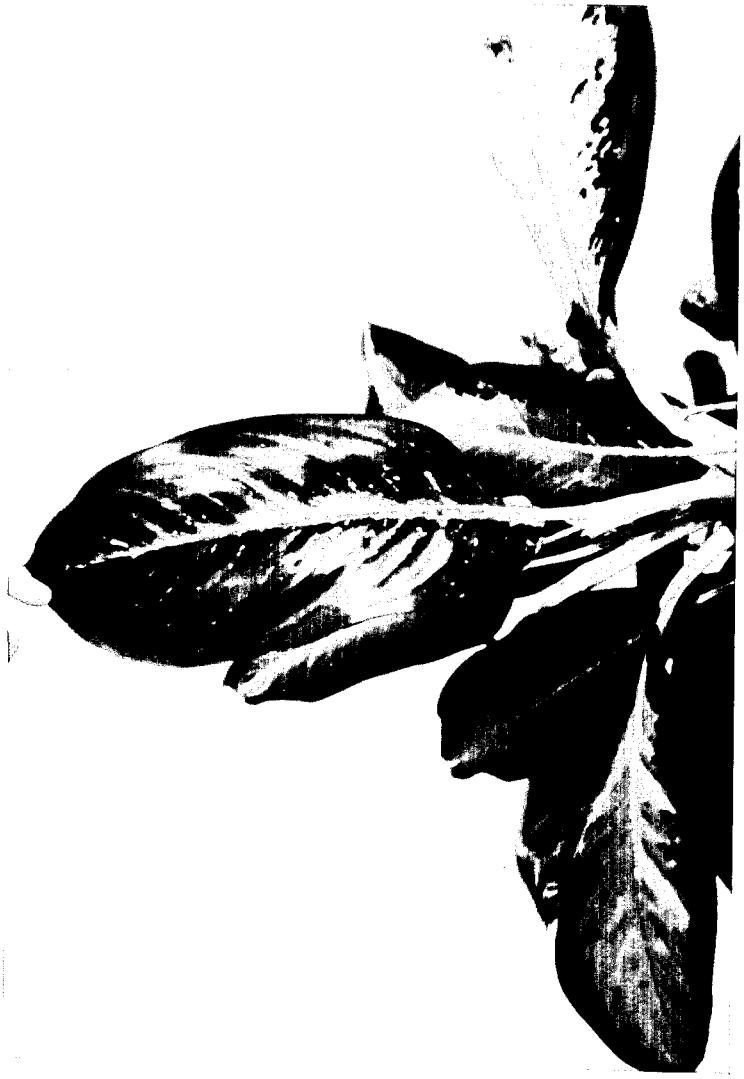
FIG. 3 is a closeup showing the under surface of mature leaves.

The following is a detailed description of the new Aglaonema plant based on observations of specimen plants grown in Valkaria, Fla. The color determinations and comparisons are all based on The Royal Horticultural Society Colour Chart.

Overall size and growth habit:

*Size.*—The ultimate size of the new variety is unknown as no plant has reached full maturity. The growth habit is compact and ascending with graceful arching leaves that become descending as they grow larger. The plant suckers freely (develops many lateral offsets). This new hybrid has grown between 10.2 cm and 15.2 cm (4 to 6 in) per year.

Foliage:

*Type.*—Evergreen, herbaceous.

*Shape.*—Broadly oblong.

*Length.*—22.9 cm to 35.6 cm (9 to 14 in).

*Width.*—10.2 cm to 15.2 cm (4 to 6 in).

*Petiole length.*—10.2 cm to 12.7 cm (4 to 5 in), generally shorter than either parent.

*Margins.*—Entire, slightly undulate.

*Apex.*—Acute to abruptly acuminate, twisted or recurved.

*Base.*—Rounded.

*Texture.*—Glabrous, semi-glossy.

*Leaf arrangement.*—Alternate.

*Venation.*—Pinnate, slightly sunken midrib and veins.

Color characteristics:

*Mature leaves upper surface.*—Central area — R.H.S. Colour Chart Fan 4, Greyed-Green Group, No. 188 C. Margin edges, blotches and spots — R.H.S. Colour Chart Fan 3, Green Group, No. 139 A. Mottling in transitional area between central zone and leaf margins — R.H.S. Colour Chart Fan 4, Greyed-Green Group, No. 189 A. Mottling and spots on midrib — R.H.S. Colour Chart Fan 3, Yellow-Green Group, No. 145 C.

*Mature leaves lower surface.*—Lower leaf surface — R.H.S. Colour Chart Fan 3, Yellow-Green Group, No. 146 A. Blotches and spots on lower leaf surface — R.H.S. Colour Chart Fan 3, Yellow-Green Group, No. 145 C. Midrib undersurface — R.H.S. Colour Chart Fan 3, Yellow-Green Group, No. 145 C. Blotches on midrib undersurface — R.H.S. Colour Chart Fan 3, Yellow-Green Group, No. 146 C. Petiole — R.H.S. Colour Chart Fan 1, Red Group, No. 36 D. Blotches on petioles — R.H.S. Colour Chart Fan 3, Yellow-Green Group, No. 145 D.

Blooming habit: Has bloomed in both spring and fall in Palm Bay, Fla. beginning in 1986.

Descriptions of Parent Plants and Differences

*Aglaonema commutatum* cv. 'Tricolor' (*A. marantifolium* var. tricolor):

*Leaf shape.*—ovate.

*Leaf length.*—12.7 cm to 24 cm (5 to 9½ in), not as long as the new selection.

*Leaf width.*—5 cm to 12.7 cm (2 to 5 in) not as wide as the new selection.

*Petioles.*—12.7 cm to 24 cm (5 to 9½ in). Pinkish.

*Leaf color.*—Upper surface is dark green with pale green blotches along primary veins. Lower surface is mottled cream along the cream colored midrib and the main veins. The variegation is extremely dissimilar when compared with the new variety.

*Aglanonema nitidum* cv. 'Curtisii':

*Leaf shape.*—Oblanceolate to oblong.

*Leaf length.*—17.8 cm to 45.7 cm (7 to 18 in).

*Leaf width.*—8.9 cm to 15.2 cm (3½ to 6 in ).

*Petioles.*—To 25.4 cm (10 in). Green, longer than the new selection.

*Leaf coloration.*—Silvery-grey variegation along the lateral leaf veins resulting in a Zebra-like appearance unlike the new selection. This plant is not a commercial cultivar because it has a slow growth rate.

Aglaonema × 'Ernesto's Favorite' (*A. nitidum* 'Curtisii' is the known parent plant):

*Leaf shape.*—Narrowly elliptic, different shape compared to the new selection.

*Leaf length.*—24.5 cm to 34 cm (9 7/10 to 13 2/5 in).

*Leaf width.*—6.8 cm to 9.7 cm (2 7/10 to 3 4/5 in).

*Petioles.*—Green with a few light green streaks.

*Leaf color.*—The upper surface central area is a silvery-green which covers about two-thirds of the leaf surface; similar to the new hybrid, the margins are dark green one-half to one inch around the entire margin; blotches and spots next to the margin area are the same color as the margin.

There are only two colors of variegation, unlike the new hybrid that has four distinct colors.

References

Bailey, L. H. & E. Z., 1976. *Hortus Third,* Macmillan, New York.

Brown, B. F., 1980. New discoveries, new hybrids, and related knowledge. *Aroideana,* Publication of the International Aroid Society 3(4): 120–126.

Brown, B. F., 1984. The new Aglaonemas of Thailand. *Aroideana* 7(2): 43–52.

Graf, A. B., 1978. *Tropica — Color Cyclopedia of Exotic Plants and Trees.* Roehrs Co., East Rutherford, N.J.

Jervis, R. N., 1987. *Florida Ornamental Plants, Aglaonema Growers Notebook.* Clearwater, Fla.

Henny, R. J., n.d. *Foliage Plant Breeding Profile* III, *Aglaonema nitidum* 'Curtisii'. Agricultural Research and Education Center. University of Florida, Apopka, Fla.

I claim:

1. A new and distinct variety of Aglaonema substantially as shown and described, characterized by:

a compact and full appearance with leaves having a four color variegation on the upper surfaces with dark green margins, also blotches and spots of this color; a light gray-green central area that occupies about 50% to 70% of the leaf surface; medium gray-green blotches and spots between the margins and central area; and bright yellow-green markings and spots on the midrib;

the lower leaf surfaces being a bright green with small yellow-green blotches and a similarly colored midrib, the midrib having small green blotches about the same as or somewhat lighter in color than the principal undersurface green.

* * * * *